US008871229B2

(12) United States Patent
Bui et al.

(10) Patent No.: US 8,871,229 B2
(45) Date of Patent: Oct. 28, 2014

(54) COSMETIC COMPOSITION FOR LONG-WEARING PROPERTIES

(75) Inventors: Hy Si Bui, Piscataway, NJ (US); Anita Tong, Westfield, NJ (US); Josselin Vazquez, Nogent-sur-Marne (FR)

(73) Assignee: L'Oreal, Paris (FR)

( * ) Notice: Subject to any disclaimer, the term of this patent is extended or adjusted under 35 U.S.C. 154(b) by 66 days.

(21) Appl. No.: 13/406,768

(22) Filed: Feb. 28, 2012

(65) Prior Publication Data
US 2013/0224130 A1 Aug. 29, 2013

(51) Int. Cl.
*A61K 9/00* (2006.01)
(52) U.S. Cl.
USPC .......................................................... 424/400
(58) Field of Classification Search
None
See application file for complete search history.

(56) References Cited

U.S. PATENT DOCUMENTS

| | | | |
|---|---|---|---|
| 2,814,601 | A | 11/1957 | Currie et al. |
| 2,857,356 | A | 10/1958 | Goodwin, Jr. |
| 2010/0260700 | A1 | 10/2010 | Dop |
| 2010/0260701 | A1 | 10/2010 | Dop |
| 2010/0310489 | A1 | 12/2010 | Barba |
| 2010/0310490 | A1 | 12/2010 | Barba et al. |
| 2010/0316587 | A1 | 12/2010 | Barba et al. |
| 2011/0002869 | A1 | 1/2011 | Barba et al. |
| 2011/0038820 | A1 | 2/2011 | Barba et al. |

FOREIGN PATENT DOCUMENTS

| | | | |
|---|---|---|---|
| EP | 0 963 751 A2 | | 12/1999 |
| JP | 09-171154 | | 6/1997 |
| WO | WO 03/045337 A2 | | 6/2003 |
| WO | WO 2005/075542 A1 | | 8/2005 |
| WO | WO 2009080960 A2 | * | 7/2009 |

OTHER PUBLICATIONS

Eastman Product Data Sheet, 2008.*
Eastman Product Data Sheet, 2013.*
English language abstract for JP-09-171154, 2009.
Smith & Kellum "Rapid Condensation Procedure for Determination of Hydroxyl in Silicone Materials," Anal. Chem., vol. 39, No. 3, Mar. 1967 (pp. 338-340).
Co-pending U.S. Appl. No. 12/746,428, filed Jun. 4, 2010; Title: Cosmetic Method Using a Composition Comprising a Siloxane Resin and a Mineral Filler; Inventor: Florence Dop.
Co-pending U.S. Appl. No. 12/746,413, filed Sep. 17, 2010; Title: Cosmetic Makeup and/or Care Process Using a Siloxane Resin and a Non-Volatile Oil; Inventor: Claudia Barba et al.
Co-pending U.S. Appl. No. 12/746,324, filed Aug. 24, 2010; Title: Cosmetic Makeup and/or Care Process Using a Siloxane Resin and a Polar Wax; Inventor: Claudia Barba et al.
Co-pending U.S. Appl. No. 12/746,613, filed Aug. 24, 2010; Title: Cosmetic Makeup and/or Care Method Using a Siloxane Resin and a Filler; Inventor: Claudia Barba et al.
Co-pending U.S. Appl. No. 12/746,282, filed Aug. 24, 2010; Title: Cosmetic Makeup and/or Care Process Using a Siloxane Resin and a Film-Forming Polymer; Inventor: Claudia Barba.
Co-pending U.S. Appl. No. 12/746,285, filed Nov. 3, 2010; Title: Cosmetic Makeup and/or Care Method Using a Siloxane Resin and a Phenyl Silicone Oil; Inventor: Claudia Barba et al.
Co-pending U.S. Appl. No. 12/746,454, filed Jun. 4, 2010; Title: Cosmetic Method Using a Composition Comprising a Siloxane Resin and a Volatile Hydrocarbon-Based Solvent; Inventor: Florence Dop.

* cited by examiner

*Primary Examiner* — Paul Dickinson
(74) *Attorney, Agent, or Firm* — The Marbury Law Group, PLLC

(57) ABSTRACT

Disclosed are cosmetic compositions comprising (1) at least one MQTPr siloxane resin; (2) at least one film former chosen from a silicone acrylate copolymer; (3) at least one film former chosen from a hydrogenated hydrocarbon copolymer; (4) at least one fatty phase; and (5) optionally at least one wax and/or colorant. Also disclosed are methods for improving at least one property of a cosmetic composition, and methods for making up and/or enhancing the appearance of keratinous substrates using compositions according to the invention.

12 Claims, No Drawings

COSMETIC COMPOSITION FOR LONG-WEARING PROPERTIES

FIELD OF THE DISCLOSURE

This disclosure relates to cosmetic compositions comprising (1) at least one MQ-T propyl siloxane resin, (2) at least one film-forming silicone acrylate copolymer, and (3) at least one film-forming hydrogenated hydrocarbon resin. Cosmetic compositions according to various embodiments of the disclosure may have improved properties, such as improved water- and/or oil-resistance, shine, malleability, adhesion, transfer resistance, comfort, and/or long wear.

BACKGROUND

There is a desire in the cosmetic industry to provide consumers with long-wearing cosmetic products having improved properties such as improved water- and/or oil-resistance, shine, malleability, adhesion, transfer resistance, and comfort. Consumers seek cosmetic products which can be applied once in the morning and worn throughout the day without requiring retouching. However, long-wearing cosmetic products tend to be brittle, difficult to apply, transfer-prone, and/or create a feeling of discomfort, such as tackiness or dryness upon application.

Cosmetic compositions containing high loads of pigments are well-known in the cosmetic field. Such compositions may provide a long wear effect; however, these compositions may be undesirable as they may be prone to color transfer.

Siloxane resins are well-known in the cosmetic field. In particular, siloxane resins belonging to the subclass known in the art as MQ resins (comprising primarily "M" units of the general formula $R_3SiO_{1/2}$ and "Q" units of the general formula $SiO_2$) are useful in cosmetic formulations. For instance, inclusion of such MQ resins in cosmetic compositions can improve various properties, such as, for example, water- and/or oil-resistance and/or long wear. However, MQ siloxane resins by themselves tend to produce cosmetics which are brittle, have poor adhesion, and feel dry and uncomfortable to the user. Therefore, in order to achieve a cosmetic composition with sufficient malleability and good adhesion properties, MQ siloxane resins are traditionally combined with a plasticizer.

MQ siloxane resins have more recently been reacted with T-Propyl ("TPr") siloxane resins (general formula $R^3SiO_{3/2}$) to produce a softer combined resin ("MQTPr") with excellent oil resistance. Such resins and their cosmetic applications are described, for example, in WO 2005/075542 and US Patent Application Publication No. 2010/0310489, the disclosures of which are incorporated herein by reference in their entireties. However, even such MQTPr resins tend to crack as a film and, when used without additives, are too brittle for cosmetic applications. Plasticizers are often added to cosmetic compositions comprising MQTPr resins so as to achieve optimal flexibility and adhesion.

Thus, there is a continuous need to provide novel cosmetic compositions which demonstrate one or more improved properties such as improved water- and/or oil-resistance, transfer resistance, adhesion, and/or long wear, and which are malleable and provide a comfortable feel to the user.

It has now been surprisingly discovered that by incorporating (1) at least one MQTPr siloxane resin, (2) at least one silicone acrylate copolymer, and (3) at least one hydrogenated hydrocarbon resin, cosmetic properties such as water- and/or oil-resistance, shine, malleability, adhesion, transfer resistance, comfort, and/or long wear can be improved.

DESCRIPTION OF EXEMPLARY EMBODIMENTS

The disclosure relates, in various embodiments, to cosmetic compositions comprising (1) at least one MQTPr siloxane resin, (2) at least one film-forming silicone acrylate copolymer, and (3) at least one film-forming hydrogenated hydrocarbon resin. In at least one exemplary embodiment, the cosmetic compositions comprise (1) at least one MQTPr siloxane resin, (2) at least one silicone acrylate copolymer, and (3) at least one hydrogenated hydrocarbon resin.

Siloxane resins useful according to the disclosure may be chosen from blends of at least one MQ resin and derivatives thereof and at least one TPr resin and derivatives thereof. According to various embodiments of the disclosure, the at least one MQTPr siloxane resin may be prepared by the following method:
(i) in a first step:
  the reaction by condensation of:
  A) at least one MQ resin (resin A) comprising at least 80 mol % of units $(R^1{}_3SiO_{1/2})_a$ and $(SiO_{4/2})_d$,
    wherein $R^1$ is chosen from alkyl groups comprising from 1 to 8 carbon atoms, aryl groups comprising from 6 to 16 carbon atoms, carbinol groups, and amino groups,
    a and d are greater than zero, and
    the ratio a/d ranges from about 0.5 to about 1.5;
  and
  B) at least one T-propyl resin (resin B) comprising at least 80 mol % of units $(R^3SiO_{3/2})_c$,
    wherein $R^3$ is chosen from alkyl groups comprising from 1 to 8 carbon atoms, aryl groups comprising from 6 to 16 carbon atoms, carbinol groups, and amino groups,
    c is greater than zero, and
    at least 40 mol % of the groups $R^3$ are propyl groups,
  wherein:
  the mass ratio A:B ranges from about 15:85 to about 95:5, and resins A and B comprise at least one free hydroxyl group,
    optionally in the presence of at least one catalyst and at least one first organic solvent chosen from aromatic hydrocarbon-based solvents;
(ii) in an optional second step:
  the addition and reaction of at least one silane terminating agent; and
(iii) in an optional third step:
  the addition of at least one second organic solvent chosen from non-aromatic oils, and
  the removal of the at least one first organic solvent.

In one exemplary embodiment, the first step may optionally include the addition of at least one additional polyorganosiloxane (component C) comprising at least one unit chosen from $R^2{}_2SiO_{2/2}$ and $R^3SiO_{3/2}$.

According to various exemplary embodiments, the radicals $R^1$, $R^2$ and $R^3$ of the MQ and TPr resins and optionally of the additional polyorganosiloxane used in the process according to the disclosure are independently chosen from alkyl groups comprising from 1 to 8 carbon atoms, aryl groups comprising from 6 to 16 carbon atoms, carbinol groups, and amino groups. Non-limiting examples of suitable alkyl groups include methyl, ethyl, propyl, butyl, pentyl, hexyl and octyl groups. In at least one embodiment, the alkyl group is chosen from methyl and propyl groups. Non-limiting examples of suitable aryl groups include phenyl, naphthyl, benzyl, tolyl, xylyl, xenyl, methylphenyl, 2-phenylethyl, 2-phenyl-2-methylethyl, chlorophenyl, bromophenyl and fluorophenyl groups. In at least one embodiment, the aryl group is a phenyl group.

As used herein, the term "carbinol group" means any group containing at least one hydroxyl radical bonded to a carbon (COH). The carbinol groups may thus comprise more than one COH radical, for instance:

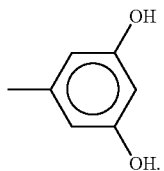

According to various embodiments, if the carbinol group is free of aryl groups, it comprises at least 3 carbon atoms. According to other embodiments, if the carbinol group comprises at least one aryl group, it comprises at least 6 carbon atoms.

Examples of carbinol groups free of aryl groups and comprising at least 3 carbon atoms include, but are not limited to, groups of formula $R^4OH$ in which $R^4$ is chosen from divalent hydrocarbon-based radicals comprising at least 3 carbon atoms and divalent hydrocarbonoxy radicals comprising at least 3 carbon atoms. Non-limiting examples of $R^4$ groups include alkylene radicals such as —$(CH_2)_x$—, wherein x ranges from 3 to 10, —$CH_2CH(CH_3)$—, —$CH_2CH(CH_3)CH_2$—, —$CH_2CH_2CH(CH_2CH_3)CH_2CH_2CH_2$—, and —$OCH(CH_3)(CH_2)_x$—, wherein x ranges from 1 to 10. Examples of carbinol groups comprising aryl groups comprising at least 6 carbon atoms include, but are not limited to, groups of formula $R^5OH$ in which $R^5$ is chosen from arylene radicals, such as —$(CH_2)_xC_6H_4$—, wherein x ranges from 0 to 10, —$CH_2CH(CH_3)(CH_2)_xC_6H_4$—, wherein x ranges from 0 to 10, and —$(CH_2)_xC_6H_4(CH_2)_x$—, wherein x ranges from 1 to 10. In at least one embodiment, carbinol groups comprising at least one aryl group may comprise from 6 to 14 atoms.

As used herein, the term "amino group" means groups of formula —$R^6NH_2$ and —$R^6NHR^7NH_2$, wherein $R^6$ and $R^7$ are independently chosen from divalent hydrocarbon-based radicals comprising at least 2 carbon atoms. According to various exemplary embodiments, the groups $R^6$ and $R^7$ may be independently chosen from alkylene radicals comprising from 2 to 20 carbon atoms. Non-limiting examples of $R^6$ and $R^7$ groups that may be mentioned include ethylene, propylene, —$CH_2CHCH_3$—, butylene, —$CH_2CH(CH_3)CH_2$—, pentamethylene, hexamethylene, 3-ethylhexamethylene, octamethylene, and decamethylene groups. In at least one exemplary embodiment, the amino groups may be chosen from —$CH_2CH_2CH_2NH_2$, —$CH_2(CH_3)CHCH_2(H)NCH_3$, —$CH_2CH_2NHCH_2CH_2NH_2$, —$CH_2CH_2NH_2$, —$CH_2CH_2NHCH_3$, —$CH_2CH_2CH_2CH_2NH_2$, —$(CH_2CH_2NH)_3H$, and —$CH_2CH_2NHCH_2CH_2NHC_4H_9$.

According to one exemplary embodiment, $R^1$ is a methyl group, $R^2$ is chosen from methyl and phenyl groups, and $R^3$ is a propyl group. In another exemplary embodiment, $R^1$ is a methyl group, $R^2$ is a methyl group, and $R^3$ is a propyl group. According to a further exemplary embodiment, the MQ and TPr resins used accordance with the present disclosure are free of D units, $R^1$ is a methyl group, and $R^3$ is a propyl group.

The First Step

Resin A is an MQ resin comprising at least 80 mol % of units $(R^1_3SiO_{1/2})_a$ and $(SiO_{4/2})_d$ (units M and Q, respectively), wherein $R^1$ is as defined above, i.e., $R^1$ is chosen from alkyl groups comprising from 1 to 8 carbon atoms, aryl groups comprising from 6 to 16 carbon atoms, carbinol groups, and amino groups, a and d are greater than 0, and the ratio a/d ranges from about 0.5 to about 1.5. The values a and d represent the mole fraction of the total number of moles of all the units M and Q, respectively, present in resin A. Thus, resin A comprises at least about 80 mol % of units M and Q, these units M and Q being present in a mole fraction respectively equal to a and d as described above. Accordingly, in at least one embodiment, the sum a+d is greater than or equal to about 0.8.

The MQ resins that may be used as resin A, and the method for preparing them, are known in the prior art. For example, U.S. Pat. No. 2,814,601, incorporated herein by reference in its entirety, describes a process for manufacturing MQ resins by transformation of a water-soluble silicate into a silicic acid monomer or a silicic acid oligomer using an acid. Once the appropriate polymerization has been performed, trimethylchlorosilane end groups are introduced to obtain the MQ resin. Another process for preparing MQ resins is described in U.S. Pat. No. 2,857,356, incorporated herein by reference in its entirety, which describes a process for manufacturing an MQ resin by cohydrolysis of a mixture of an alkyl silicate and of a water-hydrolysable trialkylsilane organopolysiloxane.

MQ resins that are suitable for use as resin A in the present disclosure may, in certain embodiments, contain at least one unit chosen from $R^2_2SiO_{2/2}$ (D units) and $R^3SiO_{3/2}$ (T units), on condition that at least about 80 mol %, for example, at least about 90 mol % of the total siloxane units are units M and Q. The MQ resin may contain at least one hydroxyl group. The MQ resin may, in certain embodiments, comprise hydroxyl groups in a total amount ranging from about 2% to about 10% by weight relative to the total weight of the MQ resin. In at least one embodiment, the MQ resin comprises hydroxyl groups in a total amount ranging from about 2% to about 5% by weight relative to the total weight of the MQ resin. The amount of hydroxyl groups present in resin A may be measured, for example, according to the method described in the article Smith & Kellum, Anal. Chem. 39 (1967) 339.

Resin B is a TPr resin comprising at least about 80 mol % of units $(R^3SiO_{3/2})_c$, wherein $R^3$ is defined above, i.e., $R^3$ is chosen from alkyl groups comprising from 1 to 8 carbon atoms, aryl groups comprising from 6 to 16 carbon atoms, carbinol groups, and amino groups, c is greater than 0, and at least 40 mol % of the groups $R^3$ are propyl groups. Thus, resin B comprises at least 80 mol % of units $R^3SiO_{3/2}$ as described previously, these units being present in a mole fraction equal to c. Accordingly, in at least one embodiment, c is greater than or equal to about 0.8.

In various exemplary embodiments, the TPr resin is chosen from silsesquioxane resins. Silsesquioxane resins are known in the prior art and may generally be obtained by hydrolysis of an organosilane comprising three hydrolysable groups, such as halogen or alkoxy groups, present in the molecule. Resin B may thus be obtained by hydrolysis of propyltrimethoxysilane, propyltriethoxysilane or propyltripropoxysilane, or by cohydrolysis of the abovementioned propylalkoxysilanes with various alkoxysilanes. Non-limiting examples of these alkoxysilanes include methyltrimethoxysilane, methyltriethoxysilane, methyltriisopropoxysilane, dimethyldimethoxysilane, and phenyltrimethoxysilane. Propyltrichlorosilane may also be hydrolyzed alone, or in the presence of alcohol. In this case, the cohydrolysis may be performed by adding methyltrichlorosilane, dimethyldichlorosilane, phenyltrichlorosilane or similar chlorosilanes and methyltrimethoxysilane, methyltriethoxysilane, methyltriisopropoxysilane or similar methylalkoxysilanes. Alcohols that are suitable for this purpose include, but are not limited to, methanol, ethanol, n-propyl alcohol, isopropyl alcohol, butanol, methoxyethanol, ethoxyethanol, and similar alcohols. Non-limiting examples of solvents of hydrocarbon type that may be used include toluene, xylene, and similar aromatic hydrocarbons; hexane, heptane, isooctane, and similar linear or partially branched saturated hydrocarbons; and cyclohexane and similar aliphatic hydrocarbons.

The TPr resin (resin B) according to the present disclosure may contain M, D and Q units, on condition that at least about 80 mol %, for example, at least about 90 mol % of the total siloxane units are T units. The TPr resin may also comprise at least one hydroxyl group. According to one embodiment, the TPr resin may comprise hydroxyl groups in a total amount ranging from about 3% to about 8% by weight of hydroxyl groups relative to the total weight of the T-propyl resin.

In various exemplary embodiments, the mass ratio of resin A:B ranges from about 20:80 to about 95:5, for example, from about 20:80 to about 90:10. For example, the mass ratio of resin A:B may be equal to about 85:15, equal to about 50:50, equal to about 30:70, or equal to about 95:5. In at least one embodiment, the mass ratio of resin A:B is equal to about 30:70.

According to various embodiments, the first step may optionally include the addition of at least one additional polyorganosiloxane (component C) comprising at least one unit chosen from $R^2_2SiO_{2/2}$ (D units) and $R^3SiO_{3/2}$ (T units). The at least one additional polyorganosiloxane may be added in order to introduce various D and T units into the MQTPr resins, so as to modify the properties of the resulting resins. The amount of component C may vary. In at least one embodiment, the addition of component C results in a content of less than about 30 mol % of additional D and/or T units, relative to the total molar amount of siloxane units in the reaction mixture.

The formula of the at least one additional polyorganosiloxane is not limiting. In certain embodiments, the at least one polyorganosiloxane comprises a measurable amount of at least one unit chosen from $R^2_2SiO_{2/2}$ and $R^3SiO_{3/2}$, and the total amount of polyorganosiloxane added to the reaction between A and B does not exceed about 50 mol % of D or T units in the reaction mixture.

In various embodiments, the polyorganosiloxane may also comprise combinations of M, D, T and Q units, with the proviso that at least the D or T units are present. Thus, the polyorganosiloxane may be chosen from fluid silicones, gums, and resins known in the art and comprising D or T units, and mixtures thereof. According to one embodiment, the D units may comprise at least one $R^2$ group chosen from methyl and phenyl groups. In another embodiment, the units T may comprise at least one $R^3$ group chosen from methyl and phenyl groups. The additional polyorganosiloxane may be a linear fluid polydiorganosiloxane having a viscosity ranging from about 10 to about 1000 cS (mm$^2$/s). The fluid polydiorganosiloxane may be chosen, in some embodiments, from polydimethylsiloxanes and polymethylphenylsiloxanes. The polyorganosiloxane may also be chosen from organosilsesquioxane resins, such as methylsilsesquioxane resins and phenylsilsesquioxane resins.

Components A, B, and optionally C as described above may react via any method known in the prior art for acting on the M, D, T and Q units. For example, in certain embodiments, components A, B, and optionally C react via a condensation reaction in the presence of a catalyst.

As described herein, components A, B, and optionally C may react in the presence of at least one catalyst and at least one first organic solvent chosen from aromatic hydrocarbon-based solvents. Non-limiting examples of aromatic hydrocarbon-based solvents include xylene and toluene.

Condensation reaction catalysts that may be used in accordance with the present disclosure include, but are not limited to, metal hydroxides such as potassium hydroxide and sodium hydroxide; metal salts such as silanolates, carboxylates, and carbonates; aqueous ammonia; amines; titanates such as tetrabutyl titanate; and mixtures thereof. In at least one embodiment, the catalyst is potassium hydroxide.

The reaction between components A, B, and optionally C may, in certain exemplary embodiments, be performed by heating the reaction mixture to temperatures ranging from about 50 to about 140° C. In at least one embodiment, the reaction temperature may range from about 100 to about 140° C. The reaction may be performed, for example, as a semi-continuous or continuous process or in batch mode.

MQTPr siloxane resins produced according to the first step as disclosed herein may comprise the following units:
(a) $(R^1_3SiO_{1/2})_a$,
(b) $(R^2_2SiO_{2/2})_b$,
(c) $(R^3SiO_{3/2})_c$, and
(d) $(SiO_{4/2})_d$,
which correspond, respectively, to the units M, D, T, and Q, wherein the amount of each unit present in the MQTPr siloxane resin may be expressed as a mole fraction (i.e., a, b, c, or d) of the total number of moles of all the units M, D, T and Q present in the MQTPr siloxane resin,
wherein $R^1$, $R^2$, and $R^3$ are independently chosen from alkyl groups comprising from 1 to 8 carbon atoms, aryl groups comprising from 6 to 16 carbon atoms, carbinol groups, and amino groups, and
wherein the sum of a+b+c+d is equal to 1.

According to various embodiments of the disclosure, the value of a (mole fraction of units M) may range from about 0.05 to about 0.5, for example, from about 0.15 to about 0.4; the value of b (mole fraction of units D) may range from about 0 to about 0.3, for example, from about 0 to about 0.1, or from about 0 to about 0.05; the value of c (mole fraction of units T) is greater than 0, for example, ranging from about 0.05 to about 0.65, or from about 0.4 to about 0.65; and the value of d (mole fraction of Q units) may range from about 0.05 to about 0.6, for example from about 0.2 to about 0.6, or from about 0.2 to about 0.55.

According to one exemplary embodiment, the value of b (mole fraction of units D) is equal to 0, such that the MQTPr siloxane resin is free of D units. In another exemplary embodiment, the value of b may be less than about 0.3.

In various embodiments of the disclosure, at least about 40 mol %, for example, at least about 50 mol %, or at least about 90 mol % of the alkyl groups $R_3$ in the T units of the MQTPr siloxane resin are propyl groups.

MQTPr siloxane resins produced according to the first step as disclosed herein may comprise at least one hydroxyl group (—OH) and/or at least one alkoxy group. For example, the D, T, or Q units of the MQTPr resin may comprise at least one hydroxyl group (—OH) and/or at least one alkoxy groups. The hydroxyl groups typically result from the reaction of a hydrolysable group on the siloxane unit with water; the alkoxy groups typically result from an incomplete hydrolysis when alkoxysilane precursors are used or result from the exchange of alcohol with hydrolysable groups.

In at least one embodiment, the total amount of —OH groups present in the MQTPr resin is less than about 3% by weight, for example, less than about 2%, or less than about 1.5%. According to another embodiment, the total amount of alkoxy groups present in the MQTPr resin is less than or equal to about 20% by weight, for example, less than or equal to about 10% by weight.

Non-limiting examples of MQTPr siloxane resins produced according to the first step as disclosed herein include:

(a) MQTPr resins comprising the following units:
$((CH_3)_3SiO_{1/2})_a$
$(R^3SiO_{3/2})_c$ in which $R^3=CH_3CH_2CH_2-$, and
$(SiO_{4/2})_d$;

(b) MQTPr resins comprising the following units:
$((CH_3)_3SiO_{1/2})_a$
$((CH_3)_2SiO_{2/2})_b$
$(R^3SiO_{3/2})_c$ in which $R^3=CH_3CH_2CH_2-$, and
$(SiO_{4/2})_d$;

(c) MQTPr resins comprising the following units:
$((CH_3)_3SiO_{1/2})_a$
$((CH_3)_2SiO_{2/2})_b$, $((CH_3)(C_6H_5)SiO_{2/2})_{b'}$
$(R^3SiO_{3/2})_c$ in which $R^3=CH_3CH_2CH_2-$, and
$(SiO_{4/2})_d$;

(d) MQTPr resins comprising the following units:
$((CH_3)_3SiO_{1/2})_a$
$((CH_3)_2SiO_{2/2})_b$
$(R^3SiO_{3/2})_c$ in which $R^3=CH_3CH_2CH_2-$, and
$(C_6H_5SiO_{3/2})_c$
$(SiO_{4/2})_d$; and (e) MQTPr resins comprising the following units:
$((CH_3)_3SiO_{1/2})_a$
$((CH_3)_2SiO_{2/2})_b$, $((CH_3)(C_6H_5)SiO_{2/2})_{b'}$
$(R^3SiO_{3/2})_c$ in which $R^3=CH_3CH_2CH_2-$, and
$(C_6H_5SiO_{3/2})_c$
$(SiO_{4/2})_d$;

wherein a has a total value in the resin ranging from about 0.05 to about 0.5, the sum b+b' has a total value in the resin ranging from about 0 to about 0.3, c has a total value in the resin ranging from about 0.05 to about 0.65, and d has a total value in the resin ranging from about 0.05 to about 0.6.

The Second Step

The preparation method disclosed herein optionally comprises the addition and reaction of at least one silane terminating agent. According to various exemplary embodiments, the at least one silane terminating agent may be chosen from monofunctional organosilanes. Non-limiting examples of monofunctional organosilanes include diorganosilanes and triorganosilanes, such as halodiorganosilanes, alkoxydiorganosilanes, carboxydiorganosilanes, halotriorganosilanes, alkoxytriorganosilanes, and carboxytriorganosilanes. Further examples of monofunctional organosilanes include, but are not limited to, chlorodimethylsilane, chlorotrimethylsilane, chlorodiphenylsilane, chlorotriphenylsilane, isopropoxydimethylsilane, isopropoxytriphenylsilane, acetoxydimethylsilane, acetoxytrimethylsilane, acetoxydiphenylsilane, and acetoxytriphenylsilane; the silanes of formulas $R'_1R'_2R'_3SiCl$, $R'_1R'_2R'_3Si(OAlk)$, and $R'_1R'_2R'_3Si(OCOAlk)$, wherein $R'_1$, $R'_2$, and $R'_3$, which may be identical or different, are independently chosen from hydrogen and organic groups, with the proviso that at least two of the groups $R'_1R'_2$ and $R'_3$ are chosen from organic groups. In at least one embodiment, the groups $R'_1R'_2$ and $R'_3$ are independently chosen from methyl and phenyl groups. According to another exemplary embodiment, the at least one silane terminating agent is chlorotrimethylsilane.

In various embodiments, the at least one silane terminating agent is added in an amount ranging from about 0.0005% to about 0.06% by weight, for example, from about 0.005% to about 0.02% by weight, relative to the total weight of the resins (A and B). According to other exemplary embodiments, the addition and the reaction of the at least one silane terminating agent are performed at a temperature ranging from about 20° C. to about 150° C., for example, from about 80° C. to about 120° C. In further embodiments, after the addition of the at least one silane terminating agent, the reaction mixture is maintained at a temperature ranging from about 60° C. to about 150° C., for about 5 to about 120 minutes, for example, for about 30 to about 60 minutes.

The Third Step

The preparation method disclosed herein optionally comprises the addition of at least one second organic solvent chosen from non-aromatic oils and the removal of the at least one first organic solvent. The third step may be performed according to the known techniques of solvent exchange in organic synthesis. For example, the at least one first aromatic organic solvent may be removed via well-known evaporation or distillation techniques.

The at least one second organic solvent may be chosen from non-aromatic oils such as, for example, non-aromatic hydrocarbon-based oils and non-aromatic silicone oils. In at least one embodiment, the non-aromatic oil is a volatile oil.

As used herein, the term "volatile oil" means an oil that is capable of evaporating on contact with keratin materials in less than one hour, at approximately room temperature and atmospheric pressure (760 mmHg). Volatile oils that may be used according to the disclosure include, but are not limited to, volatile cosmetic oils, which are liquid at room temperature and have a non-zero vapor pressure at room temperature and atmospheric pressure, said vapor pressure ranging, for example, from about 0.13 Pa to about 40,000 Pa ($10^{-3}$ to 300 mmHg), such as from about 1.3 Pa to about 13,000 Pa (0.01 to 100 mmHg), or from about 1.3 Pa to about 1,300 Pa (0.01 to 10 mmHg). In contrast, non-volatile oils have a vapor pressure of less than about 1.33 Pa (0.01 mmHg).

According to various embodiments, the non-aromatic hydrocarbon-based oils may be chosen from:

hydrocarbon-based oils comprising from 8 to 16 carbon atoms, for example, $C_8$-$C_{16}$ branched alkanes such as $C_8$-$C_{16}$ isoalkanes of petroleum origin (also known as isoparaffins), for instance isododecane (also known as 2,2,4,4,6-pentamethylheptane), isodecane, and isohexadecane, and, for example, the oils sold under the trade names Isopar® and Permethyl®; linear alkanes, for instance, n-dodecane (C12) and n-tetradecane (C14) sold by Sasol under the respective references Parafol 12-97 and Parafol 14-97, and mixtures thereof; the undecane-tridecane mixture, and mixtures of n-undecane (C11) and of n-tridecane (C13) obtained in Examples 1 and 2 of International Patent Application Publication No. WO 2008/155 059 assigned to the company Cognis, and mixtures thereof;

linear and branched hydrocarbons of mineral or synthetic origin, such as petroleum jelly, polydecenes, hydrogenated polyisobutene such as Parleam®, squalane, liquid paraffins, and mixtures thereof;

synthetic esters such as oils of formula $R'_{1000}R'_2$ in which $R'_1$ is chosen from linear and branched fatty acid residues comprising from 1 to 40 carbon atoms and $R'_2$ is chosen from branched hydrocarbon-based chains comprising from 1 to 40 carbon atoms, with the proviso that $R'_1$+$R'_2$ 10, for instance purcellin oil (cetostearyl octanoate), isopropyl myristate, isopropyl palmitate, $C_{12}$ to $C_{15}$ alkyl benzoate, hexyl laurate, diisopropyl adipate, isononyl isononanoate, 2-ethylhexyl palmitate, isostearyl isostearate, 2-hexyldecyl laurate, 2-octyldecyl palmitate, 2-octyldodecyl myristate, alkyl and polyalkyl heptanoates, octanoates, decanoates, and ricinoleates such as propylene glycol dioctanoate; hydroxylated esters such as isostearyl lactate, diisostearyl malate, and 2-octyldodecyl lactate; polyol esters and pentaerythritol esters; fatty alcohols that are liquid at room temperature, comprising a branched and/or unsaturated carbon-based chain comprising from 12 to 26 carbon atoms, for instance, octyldodecanol, isostearyl alcohol, oleyl alcohol, 2-hexyldecanol, 2-butyloctanol, and 2-undecylpentadecanol;

higher fatty acids such as oleic acid, linoleic acid, linolenic acid, and mixtures thereof; and hydrocarbon-based oils of plant origin such as triglycerides comprising fatty acid esters of glycerol, the fatty acids of which may have chain lengths comprising from 4 to 24 carbon atoms, these chains possibly being linear or branched, and saturated or unsaturated; for example, heptanoic and octanoic acid triglycerides, wheatgerm oil, sunflower oil, grapeseed oil, sesame seed oil, corn oil, apricot oil, castor oil, shea oil, avocado oil, olive oil, soybean oil, sweet almond oil, palm oil, rapeseed oil, cottonseed oil, hazelnut oil, macadamia oil, jojoba oil, alfalfa oil, poppy oil, pumpkin oil, marrow oil, blackcurrant oil, evening primrose oil, millet oil, barley oil, quinoa oil, rye oil, safflower oil, candlenut oil, passion flower oil, and musk rose oil; shea butter; and caprylic/capric acid triglycerides, for instance those sold by the company Stéarineries Dubois or those sold under the names Miglyol 810®, 812® and 818® by the company Dynamit Nobel.

In various embodiments of the disclosure, the non-volatile silicone oils may be chosen from volatile linear or cyclic silicone oils, for example, silicone oils with a viscosity ≤about 5 centistokes ($5\times10^{-6}$ m$^2$/s), and, in some embodiments, comprising from 2 to 10 silicon atoms, such as from 2 to 7 silicon atoms, these silicones optionally comprising at least one group chosen from alkyl and alkoxy groups comprising from 1 to 10 carbon atoms. Non-limiting examples of volatile silicone oils that may be used in accordance with the disclosure include octamethylcyclotetrasiloxane, decamethylcyclopentasiloxane, dodecamethylcyclohexasiloxane, heptamethylhexyltrisiloxane, heptamethyloctyltrisiloxane, hexamethyldisiloxane, octamethyltrisiloxane, decamethyltetrasiloxane, dodecamethylpentasiloxane, and mixtures thereof.

According to one exemplary embodiment, the at least one non-aromatic oil is chosen from hydrocarbon-based oils comprising from 8 to 16 carbon atoms. For example, in at least one embodiment, the non-aromatic oil is isododecane.

According to various embodiments of the disclosure, the at least one MQTPr siloxane resin may be chosen from those having an MQ:TPr ratio ranging from about 15:85 to about 95:5, for example, from about 70:30 to about 30:70, or from about 60:40 to about 40:60. In at least one exemplary embodiment of the disclosure, the MQ:TPr ratio is about 30:70. In other embodiments of the disclosure, the number-average molecular mass ($M_N$) of the at least one MQTPr siloxane resin ranges from about 3,000 to about 10,000 g/mol. In at least one exemplary embodiment of the disclosure, the number-average molecular mass ranges from about 5,000 to about 8,000 g/mol.

In various exemplary embodiments, the at least one MQTPr resin may be present in the cosmetic composition in an amount ranging from about 5% to about 50% by weight, such as from about 10% to about 40%, or from about 15% to about 30%. In at least one exemplary embodiment of the disclosure, the at least one MQTPr resin is present in the cosmetic composition in an amount ranging from about 6% to about 30% by weight, such as from about 9% to about 21%.

As described herein, the cosmetic compositions further comprise at least one silicone acrylate copolymer. Silicone acrylate copolymers useful according to various embodiments of the disclosure include one or more silicone dendrimer grafted acrylate copolymers and derivatives thereof, such as, for example, copolymers comprising at least one carbosiloxane dendrimer structure grafted onto a vinyl backbone. As used herein, the expression "carbosiloxane dendrimer structure" denotes a structure with branched groups of high molecular mass with high regularity in the radial directions starting from the vinyl backbone. Such carbosiloxane dendrimer structures are described, for example, in Japanese Patent Application Kokai 9-171 154.

In at least one exemplary embodiment, the at least one carbosiloxane dendrimer structure is chosen from those of general formula (I):

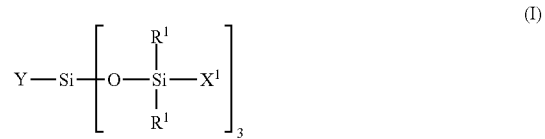

wherein:

$R^1$ is chosen from aryl groups comprising from 1 to 10 carbon atoms and alkyl groups comprising from 1 to 10 carbon atoms;

$X^1$ is chosen from silylalkyl groups of general formula (II), where i=1:

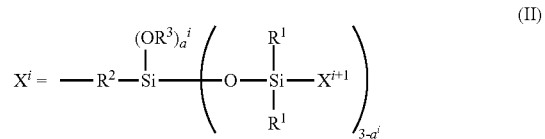

wherein:

$R^1$ is chosen from aryl groups comprising from 1 to 10 carbon atoms and alkyl groups comprising from 1 to 10 carbon atoms;

$R^2$ is chosen from alkylene groups comprising from 2 to 10 carbon atoms;

$R^3$ is chosen from alkyl groups comprising from 1 to 10 carbon atoms;

$X^{i+1}$ is chosen from hydrogen, alkyl groups comprising from 1 to 10 carbon atoms, aryl groups, and silalkyl groups of formula (II) above, where i=i+1; and i is an integer ranging from 1 to 10 which represents the generation of the silalkyl group; and Y is chosen from organic groups comprising at least one group chosen from (meth)acrylic and acrylic groups of general formulas (III) and (IV):

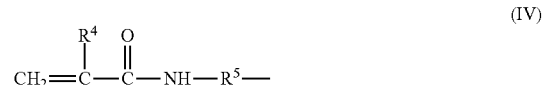

wherein:

$R^4$ is chosen from hydrogen and alkyl groups, such as methyl groups; and $R^5$ is chosen from alkylene groups comprising from 1 to 10 carbon atoms, such as methylene, ethylene, propylene, and butylene groups, and organic groups comprising at least one styryl group of general formula (V):

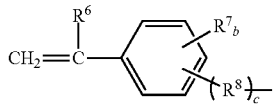

wherein:

$R^6$ is chosen from hydrogen and alkyl groups, such as methyl groups;

$R^7$ is chosen from alkyl groups comprising from 1 to 10 carbon atoms, such as methyl, ethyl, propyl, and butyl groups;

$R^8$ is chosen from alkylene groups comprising from 1 to 10 carbon atoms, such as methylene, ethylene, propylene, and butylene groups;

b is an integer ranging from 0 to 4; and c is 0 or 1, such that if c is 0, —$(R^8)_c$— represents a bond.

According to various embodiments of the disclosure, the at least one carbosiloxane dendrimer may be prepared according to the process described in Japanese Patent Application Hei 9-171 154.

By way of non-limiting example only, the at least one silicone acrylate copolymer may be chosen from those disclosed in European Patent No. 0 963 751 and International Patent Application No. WO 03/045337, the disclosures of which are incorporated herein by reference in their entireties. According to various embodiments of the disclosure, the at least one silicone acrylate copolymer is chosen from, for example, acrylate/polytrimethylsiloxymethacrylate copolymers, acrylate/dimethicone copolymers, and derivatives thereof.

Exemplary commercially available silicone acrylate copolymer products that may be used include, but are not limited to, acrylate/polytrimethylsiloxymethacrylate copolymer products sold by Dow Chemical Company, such as, for example, FA 4002 ID Silicone Acrylate and FA 4001 CM Silicone Acrylate, and acrylate/dimethicone copolymer products sold by Shin-Etsu Chemical Company, such as, for example, KP-550, KP-541, KP-543, KP-545, KP-549, KP-561P, and KP-562P.

In various embodiments, the at least one silicone acrylate copolymer may be present in the cosmetic composition in an amount ranging from about 0.1% to about 10% by weight, such as from about 0.5% to about 8.5%, or from about 1% to about 7%. In at least one exemplary embodiment of the disclosure, the at least one silicone acrylate copolymer may be present in an amount ranging from about 0.1% to about 10%, such as from about 1% to about 5%.

The cosmetic compositions described herein further comprise at least one hydrogenated hydrocarbon resin. Hydrogenated hydrocarbon resins useful according to various embodiments of the disclosure include, by way of example only, one or more chosen from hydrogenated styrene/methyl styrene/indene copolymers, hydrogenated polycyclopentadienes, and derivatives thereof.

Exemplary commercially available hydrogenated hydrocarbon resin products that may be used include, but are not limited to, products sold by Eastman Chemical Company under the trade name Regalite™, e.g., R1090, R1100, R7100, S1100, and S5100; products sold by Eastman Chemical Company under the trade names Eastotac™ and Regalrez™, e.g., Regalrez™ 1085; and products sold by Kobo Products under the trade name Koboguard®, e.g., Koboguard® 5400 IDD.

According to various embodiments of the disclosure, the molecular weight of the at least one hydrogenated hydrocarbon resin may range from about 500 to about 1500, such as, for example, from about 600 to about 1200, or from about 700 to about 900. In at least one exemplary embodiment of the disclosure, the molecular weight ranges from about 500 to about 900.

In various embodiments, the at least one hydrogenated hydrocarbon resin may be present in the cosmetic composition in an amount ranging from about 1% to about 25% by weight, such as from about 5% to about 20%, or from about 10% to about 15%. In at least one exemplary embodiment of the disclosure, the at least one hydrogenated hydrocarbon resin may be present in an amount ranging from about 1% to about 15% by weight, such as from about 3% to about 10%.

In accordance with various embodiments of the disclosure, the weight ratio of the at least one MQTPr siloxane resin to the at least one silicone acrylate copolymer to the at least one hydrogenated hydrocarbon resin, respectively, is about 8:1:1. In another exemplary embodiment, the weight ratio is about 7:2:1. In a further exemplary embodiment, the weight ratio is about 6.5:2.5:1.

In various embodiments, the amounts of silicone acrylate copolymer, hydrogenated hydrocarbon, and siloxane resin are chosen such that they are present in the composition in a ratio relative to each other. For example, the weight ratio of the at least one silicone acrylate copolymer to the at least one MQTPr siloxane resin may range from about 1:8 to about 1:5.5, such as from about 1:7 to about 1:6. The weight ratio of the at least one hydrogenated hydrocarbon resin to the MQTPr siloxane resin may range from about 1:5 to about 1:1.5, such as from about 1:4 to about 1:3. In one exemplary embodiment, the weight ratio of the hydrogenated styrene/methyl styrene/indene copolymer to the MQTPr siloxane resin may range from about 1:5 to about 1:1.5, such as from about 1:4 to about 1:3. In a further exemplary embodiment, the weight ratio of the hydrogenated polycyclopentadiene to the MQTPr siloxane resin may range from about 1:5 to about 1:1.5, such as from about 1:4 to about 1:3. The weight ratio of the at least one hydrogenated hydrocarbon resin to the at least one silicone acrylate copolymer may range from about 1:1 to about 4:1, such as from about 2:1 to about 3:1. As used herein, weight ratio is meant to describe the ratio of the active amount of each component by weight.

According to at least one embodiment, the amounts of the at least one silicone acrylate copolymer and the at least one hydrogenated hydrocarbon resin are chosen such that the combined weight of these two components does not exceed the weight of the at least one MQTPr siloxane resin. For example, the weight ratio of MQTPr siloxane resin to the combined amount of (silicone acrylate copolymer+hydrogenated hydrocarbon resin) is greater than about 1.

In various embodiments of the disclosure, the total solid content of the cosmetic compositions described herein may range from about 10% to about 80% by weight, such as from about 20% to about 70%, or from about 30% to about 60%, or from about 35% to about 50%. In at least one exemplary embodiment, the total solid content ranges from about 10% to about 50%. In at least one further exemplary embodiment, the total solid content is less than about 50%.

One embodiment of the disclosure relates to cosmetic compositions comprising (1) at least one MQTPr siloxane resin, (2) at least one silicone acrylate polymer chosen from acrylate/polytrimethylsiloxymethacrylate copolymers, acrylate/dimethicone copolymers, and derivatives thereof, and (3) at least one hydrogenated hydrocarbon chosen from hydrogenated styrene/methyl styrene/indene copolymer, hydrogenated polycyclopentadienes, and derivatives thereof.

Another exemplary embodiment of the disclosure relates to cosmetic compositions comprising (1) at least one MQTPr siloxane resin, (2) at least one acrylate/polytrimethylsiloxymethacrylate copolymer, such as, for example, Dow Corning® FA 4002 ID, and (3) at least one hydrogenated styrene/methyl styrene/indene copolymer, such as, for example, Regalite™ R1100 CG Hydrogenated Hydrocarbon Resin.

A further exemplary embodiment of the disclosure relates to cosmetic compositions comprising (1) at least one MQTPr siloxane resin, (2) at least one acrylate/polytrimethylsiloxymethacrylate copolymer, such as, for example, Dow Corning® FA 4002 ID, and (3) at least one hydrogenated polycyclopentadiene, such as, for example, Koboguard® 5400 IDD.

Yet another embodiment of the disclosure relates to cosmetic compositions comprising (1) at least one MQTPr siloxane resin, (2) at least one acrylate/dimethicone copolymer, such as, for example, KP-550, and (3) at least one hydrogenated styrene/methyl styrene/indene copolymer, such as, for example, Regalite™ R1100 CG Hydrogenated Hydrocarbon Resin.

Another embodiment of the disclosure relates to cosmetic compositions comprising (1) at least one MQTPr siloxane resin, (2) at least one acrylate/dimethicone copolymer, such as, for example, KP-550, and (3) at least one hydrogenated polycyclopentadiene, such as, for example, Koboguard® 5400 IDD.

In various embodiments, the composition according to the disclosure comprises at least one liquid fatty phase comprising at least one oil. The at least one oil may be chosen from volatile oils, non-volatile oils, and mixtures thereof, including, for example, hydrocarbon-based oils, silicone oils and fluoro oils.

The term "hydrocarbon-based oil" means an oil formed essentially from, or even consisting of, carbon and hydrogen atoms, and possibly oxygen and nitrogen atoms, and containing no silicon or fluorine atoms; it may contain ester, ether, amine or amide groups. The term "silicone oil" means an oil containing at least one silicon atom, and especially containing Si—O groups. The term "fluoro oil" means an oil containing at least one fluorine atom.

The term "volatile oil" means an oil capable of evaporating on contact with the skin in less than one hour, at room temperature and atmospheric pressure. The volatile oils may be volatile cosmetic oils, liquid at room temperature, such as those having a non-zero vapour pressure, at room temperature and atmospheric pressure, for example having a vapour pressure ranging from about 0.13 Pa to about 40,000 Pa (about $10^{-3}$ to about 300 mmHg), such as from about 1.3 Pa to about 13,000 Pa (about 0.01 to about 100 mmHg), or from about 1.3 Pa to about 1300 Pa (about 0.01 to about 10 mmHg). In addition, the volatile oils may have a boiling point, measured at atmospheric pressure, ranging from about 150° C. to about 260° C., such as from about 170° C. to about 250° C.

The composition may comprise at least one volatile hydrocarbon-based oil chosen from, for example, hydrocarbon-based oils with a flash point ranging from about 40° C. to about 102° C., such as from about 40° C. to about 55° C., such as from about 40° C. to about 50° C.

Volatile hydrocarbon-based oils that may be used include, in various embodiments, volatile hydrocarbon-based oils containing from 8 to 16 carbon atoms and mixtures thereof, and especially branched $C_8$-$C_{16}$ alkanes, for instance $C_8$-$C_{16}$ isoalkanes (also known as isoparaffins), isododecane, isodecane, isohexadecane, isohexyl neopentanoate, branched $C_8$-$C_{16}$ esters, and mixtures thereof. For example, the oils sold under the trade names Isopar or Permethyl may be chosen.

Volatile silicone oils that may be used include, in various embodiments, linear or cyclic silicones containing from 2 to 7 silicon atoms, optionally comprising alkyl or alkoxy groups containing from 1 to 10 carbon atoms. By way of non-limiting example only, octamethylcyclotetrasiloxane, decamethylcyclopentasiloxane, dodecamethylcyclohexasiloxane, heptamethyl-hexyltrisiloxane, heptamethyloctyltrisiloxane, octamethyltrisiloxane and decamethyltetrasiloxane, and mixtures thereof may be chosen.

The volatile oil may be present in the composition according to the invention in a content ranging from about 0.1% to about 90% by weight, such as from about 1% to about 70% by weight, or from about 5% to about 50% by weight, relative to the total weight of the composition.

In various embodiments, the fatty phase may comprise at least one non-volatile oil. Non-volatile oils may be chosen from, for example, non-volatile hydrocarbon-based oils and non-volatile silicone oils. Non-volatile hydrocarbon-based oils that may be used include, but are not limited to, liquid paraffin (or petroleum jelly), squalane, hydrogenated polyisobutylene (Parleam oil), perhydrosqualene, mink oil, turtle oil, soybean oil, sweet almond oil, beauty-leaf oil, palm oil, grapeseed oil, sesame seed oil, corn oil, arara oil, rapeseed oil, sunflower oil, cottonseed oil, apricot oil, castor oil, avocado oil, jojoba oil, olive oil or cereal germ oil; linoleic acid, oleic acid, lauric acid or stearic acid esters; fatty esters, e.g. $C_{12}$-$C_{36}$, such as isopropyl myristate, isopropyl palmitate, butyl stearate, hexyl laurate, diisopropyl adipate, isononyl isononanoate, 2-ethylhexyl palmitate, 2-hexyldecyl laurate, 2-octyldecyl palmitate, 2-octyldodecyl myristate or lactate, bis(2-ethylhexyl)succinate, diisostearyl malate, and glyceryl or diglyceryl triisostearate; behenic acid, oleic acid, linoleic acid, linolenic acid or isostearic acid; higher fatty alcohols, e.g. $C_{16}$-$C_{22}$, such as cetanol, oleyl alcohol, linoleyl alcohol, linolenyl alcohol, isostearyl alcohol or octyldodecanol; and mixtures thereof.

The non-volatile oils may be present in an amount ranging from about 0.1% to about 70% by weight, such as from about 0.5% to about 60%, or from about 1% to about 50% by weight relative to the total weight of the non-volatile liquid fatty phase.

In addition, other cosmetic ingredients may optionally be included in the compositions according to the disclosure. Such ingredients are known, and include but are not limited to solvents (including water), waxes, colorants, humectants, emulsifiers, surfactants, preservatives, fragrances, thickeners or texturizers, emollients, and additional film-formers, coalescents, and/or plasticizers. Exemplary additional cosmetic ingredients may be chosen, for example, from those described in U.S. Patent Application Publication No. 2010/0310148, incorporated by reference herein. One of skill in the art will be able to select appropriate types and amounts of additional cosmetic ingredients, based on, for example, the type of cosmetic composition being formulated and the desired properties thereof. By way of example only, such additional cosmetic ingredients may be present in the compositions according to the disclosure in a combined amount ranging from about 10% to about 80% by weight, such as about 15% to about 60%, about 25% to about 40%, or about 30% to about 35%.

Exemplary cosmetic compositions contemplated according to the disclosure include compositions intended for application to keratinous substrate, such as the hair, skin, and nails.

Such compositions include, but are not limited to, nail compositions (e.g. nail enamel), mascara compositions, make-up compositions (e.g. foundations and lipsticks), sunscreen compositions, and hair-care compositions (e.g. hair-styling compositions). Thus, further embodiments relate to methods of making up and/or enhancing the appearance of at least one keratinous substrate, comprising applying a cosmetic composition as described herein to the keratinous substrate.

Also disclosed herein is a method of improving at least one property chosen from water- and/or oil-resistance, shine, malleability, adhesion, transfer resistance, comfort, and long wear properties in a cosmetic composition, said method comprising including in the cosmetic composition (1) at least one MQTPr siloxane resin, (2) at least one silicone acrylate copolymer, and (3) at least one hydrogenated hydrocarbon resin.

Without wishing to be bound by theory, it is believed that the combination of at least one MQTPr siloxane resin, at least one silicone acrylate copolymer, and at least one hydrogenated hydrocarbon resin as described herein surprisingly and unexpectedly shows a synergistic effect, imparting improved properties such as, for example, improved water- and/or oil-resistance, shine, malleability, adhesion, transfer resistance, comfort, and/or long wear to the cosmetic compositions. In addition, the at least one MQTPr siloxane resin, at least one silicone acrylate copolymer, and at least one hydrogenated hydrocarbon resin, when combined in specific ratios, work synergistically to achieve unexpectedly optimal properties such as, for example, improved water- and/or oil-resistance, shine, malleability, adhesion, transfer resistance, comfort, and/or long wear to the cosmetic compositions. Furthermore, inclusion of at least one MQTPr siloxane resin, at least one silicone acrylate copolymer, and at least one hydrogenated hydrocarbon resin in a cosmetic composition provides a synergistic effect resulting in a composition with improved malleability and flexibility and may, in certain embodiments, eliminate the need to include a plasticizer in the cosmetic composition.

By way of example only, solid lip color formulations comprising at least one MQTPr siloxane resin, at least one silicone acrylate copolymer, and at least one hydrogenated hydrocarbon resin as described herein have been found to have improved color transfer resistance, comfort, and long wear properties. As a further non-limiting example, liquid lip color formulations comprising at least one MQTPr siloxane resin, at least one silicone acrylate copolymer, and at least one hydrogenated hydrocarbon resin as described herein have been found to have improved oil resistance, comfort, and long wear properties. It should be noted, however, that compositions according to the disclosure may not have one or more of the above-referenced improved properties, yet such compositions are intended to be within the scope of the disclosure.

It is to be understood that both the foregoing description and the following Examples are exemplary and explanatory only, and are not to be interpreted as restrictive of the disclosure. Moreover, it should be understood that various features and/or characteristics of differing embodiments herein may be combined with one another. It is therefore to be understood that numerous modifications may be made to the illustrative embodiments and that other arrangements may be devised without departing from the scope of the invention. Other embodiments will be apparent to those skilled in the art from consideration of the disclosure and practice of the various exemplary embodiments disclosed herein.

It is also to be understood that, as used herein the terms "the," "a," or "an," mean "at least one," and should not be limited to "only one" unless explicitly indicated to the contrary. Thus, for example, the use of "a silicone acrylate copolymer" is intended to mean at least one silicone acrylate copolymer.

Unless otherwise indicated, all numbers used in the specification and claims are to be understood as being modified in all instances by the term "about," whether or not so stated. It should also be understood that the precise numerical values used in the specification and claims form additional embodiments of the invention, and are intended to include any ranges which can be narrowed to any two end points disclosed within the exemplary ranges and values provided. Efforts have been made to ensure the accuracy of the numerical values disclosed herein. Any measured numerical value, however, can inherently contain certain errors resulting from the standard deviation found in its respective measuring technique.

EXAMPLES

The following Examples are intended to be non-restrictive and explanatory only, with the scope of the invention being defined by the claims.

Example 1

Lip Color Compositions

Five lip color compositions were prepared by mixing, independently, using moderate agitation at room temperature for 15 minutes, the components set forth in the following Table I. Inventive compositions A and B, in accordance with the disclosure, comprise at least one MQTPr siloxane resin, at least one silicone acrylate copolymer, and at least one hydrogenated hydrocarbon resin. Comparative compositions C and D, not in accordance with the disclosure, comprise at least one MQTPr siloxane resin and at least one hydrogenated hydrocarbon resin, but do not comprise at least one silicone acrylate copolymer. Comparative composition E, not in accordance with the disclosure, comprises at least one MQTPr siloxane resin and at least one silicone acrylate copolymer, but does not comprise at least one hydrogenated hydrocarbon resin.

TABLE I

Preparation of Lip Color Compositions A-E

| COMPONENT | WEIGHT % | | | | |
|---|---|---|---|---|---|
| | Composition A (Inventive) | Composition B (Inventive) | Composition C (Comparative) | Composition D (Comparative) | Composition E (Comparative) |
| HYDROGENATED STYRENE/METHYL STYRENE/INDENE COPOLYMER | 5 | | 5 | | |

TABLE I-continued

Preparation of Lip Color Compositions A-E

| COMPONENT | WEIGHT % | | | | |
|---|---|---|---|---|---|
| | Composition A (Inventive) | Composition B (Inventive) | Composition C (Comparative) | Composition D (Comparative) | Composition E (Comparative) |
| HYDROGENATED POLYCYCLO PENTADIENE | | 5 | | 5 | |
| ACRYLATES/POLY TRIMETHYLSILOXY METHACRYLATE COPOLYMER | 2 | 2 | | | 5 |
| MQTPr RESIN | 13 | 13 | 13 | 13 | 13 |
| COLOR PIGMENTS | 1 | 1 | 1 | 1 | 1 |
| ISODODECANE | 79 | 79 | 81 | 81 | 81 |

Each composition was observed for solution stability, resistance to oil, and resistance to rubbing/wear. These observations are set forth in Table II.

Solution stability was evaluated based on observations of the bulk compositions after storage at room temperature for about one month. To evaluate resistance to oil and rubbing/wear, films of each composition were prepared by casting the solutions on pre-cut opacity charts. The films were dried for 24 hours at about 20° C. and a relative humidity of about 45% to a thickness of about 30 μm. The resistance of each composition to oil was observed by depositing several drops of olive oil on each film and removing the oil from the film at approximately 5 minute increments up to about 45 minutes. The films were evaluated for oil resistance by observing at what time the surface was destroyed or removed during the removal of the oil. The resistance of each composition to rubbing/wear was observed by stroking the films with a steel ball (diameter ranging from about 5 mm to about 10 mm) at a normal force ranging from about 0.5N to about 2N and a speed ranging from about 10 to about 50 mm/s. The films were evaluated for rubbing/wear resistance by observing at what number of strokes the substrate beneath the film became visible.

TABLE II

Evaluation of Compositions A-E

| Property | Composition A (Inventive) | Composition B (Inventive) | Composition C (Comparative) | Composition D (Comparative) | Composition E (Comparative) |
|---|---|---|---|---|---|
| Solution Stability | Yes | Yes | Yes | Partial | No |
| Resistance to Oil | >45 min | >45 min | >45 min | >45 min | 10-15 min |
| Resistance to Rubbing/Wear | 50-100 | 30-50 | 20-30 | 20-30 | 50-100 |

Inventive compositions A and B performed well in all three tests. Namely, inventive compositions A and B exhibited excellent solution stability, resistance to oil, and resistance to rubbing/wear. In contrast, comparative composition C (not comprising at least one silicone acrylate copolymer) exhibited diminished resistance to rubbing/wear as compared to the inventive compositions. Comparative composition D (not comprising at least one silicone acrylate copolymer) exhibited both diminished solution stability and diminished resistance to rubbing/wear as compared to the inventive compositions. Comparative composition E (not comprising at least one hydrogenated hydrocarbon resin) exhibited both diminished solution stability and diminished resistance to oil as compared to the inventive compositions.

Example 2

Lipstick Compositions

Two solid cosmetic compositions were prepared by combining, independently, the components set forth in the following Table III. Inventive compositions F and G, in accordance with the disclosure, comprise at least one MQTPr siloxane resin, at least one silicone acrylate copolymer, and at least one hydrogenated hydrocarbon resin.

Compositions F and G were prepared as follows: Waxes were added to a container of suitable size and heated to about 80° C. until all waxes were melted and uniform. Subsequently, all components except the color pigments and fillers were added to the container with moderate agitation and mixed at about 80° C. for about 15 minutes until uniform. The color pigments and fillers were then added to the container and mixed for about 5 minutes. The resulting compositions were poured into lipstick molds. The compositions were then placed in a cooling tunnel for about 15 minutes at −10° C. Once cooled, the compositions were removed from the cooling tunnel, equilibrated to 25° C., and then removed from the molds. The compositions were stored in proper packaging until evaluation.

TABLE III

Preparation of Lipstick Compositions F and G

| COMPONENT | | WEIGHT % | |
|---|---|---|---|
| INCI | Trade Name | Composition F (Inventive) | Composition G (Inventive) |
| TRIMETHYL-SILOXYPHENYL DIMETHICONE | BELSIL PDM 1000 | 40 | 40 |
| WAXES | | 17 | 17 |
| COLOR PIGMENTS/FILLERS | | 12 | 12 |
| MQTPr RESIN (60% solids in isododecane) | | 19 | 19 |

TABLE III-continued

Preparation of Lipstick Compositions F and G

|  |  | WEIGHT % | |
|---|---|---|---|
| COMPONENT | | Composition F | Composition G |
| INCI | Trade Name | (Inventive) | (Inventive) |
| HYDROGENATED STYRENE/METHYL STYRENE/INDENE COPOLYMER | REGALITE™ R1100 CG | 3.8 | |
| HYDROGENATED POLYCYCLO-PENTADIENE | KOBOGUARD® 5400 IDD (70% active in isododecane) | | 5.43 |
| ACRYLATES/ POLYTRIMETHYL SILOXY-METHACRYLATE COPOLYMER | DOW CORNING® FA 4002 ID (40% active in isododecane) | 3.8 | 3.8 |
| ISODODECANE | | Q.S. | Q.S. |

Example 3

Lip Color Compositions

Three liquid cosmetic compositions were prepared by mixing, independently, using moderate agitation at about 65° C. for about 15 minutes, the components set forth in the following Table IV. Inventive composition J, in accordance with the disclosure, comprises at least one MQTPr siloxane resin, at least one silicone acrylate copolymer, and at least one hydrogenated hydrocarbon resin. Comparative composition H, not in accordance with the disclosure, comprises at least one MQTPr siloxane resin, but does not comprise at least on hydrogenated hydrocarbon resin or at least one silicone acrylate copolymer. Comparative composition I, not in accordance with the disclosure, comprises at least one MQTPr siloxane resin and at least one hydrogenated hydrocarbon resin, but does not comprise at least one silicone acrylate copolymer.

Each of compositions H-J was applied to the forearms of three test subjects with the same force for five strokes. Each composition was evaluated for resistance to oil, adhesion to the skin, and flaking. These observations are set forth in Table V, where each number listed represents the average result for the three test subjects.

Resistance to oil was evaluated as follows: the compositions were allowed to dry on the arm for ten minutes before a drop of olive oil was applied to each patch of color. The olive oil was allowed to remain on the arm for five minutes before the area was rubbed with a Kimwipe five times. The Kimwipe was visually evaluated for color transfer and rated on a scale from 0 to 5, where 0 represents high color transfer (no oil resistance) and 5 represents no color transfer (high oil resistance) and 5 is most preferred.

Flaking was evaluated as follows: the compositions were allowed to dry on the arm for ten minutes before the area was rubbed with a Kimwipe five times. Flaking on the Kimwipe was visually evaluated and rated on a scale from 0 to 5, where 0 represents high flaking and 5 represents no flaking and 5 is most preferred.

Adhesion was evaluated as follows: the compositions were allowed to dry on the arm for ten minutes before the area was rubbed with a Kimwipe. The treated area was visually evaluated for color adhesion to the skin and rated on a scale of 0 to 5, where 0 represents no adhesion and 5 represents high adhesion and 5 is most preferred.

TABLE V

Evaluation of Compositions H-J

| Property | Composition H (Comparative) | Composition I (Comparative) | Composition J (Inventive) |
|---|---|---|---|
| Resistance to Oil | 4 | 4 | 4 |
| Adhesion | 2 | 3 | 5 |
| Flaking | 0 | 2 | 3.5 |

Inventive composition J exhibited improved adhesion and reduced flaking as compared to comparative compositions H and I, while also maintaining excellent oil resistance.

TABLE IV

Preparation of Lip Color Compositions H-J

|  |  | WEIGHT % | | |
|---|---|---|---|---|
| COMPONENT | | Composition H | Composition I | Composition J |
| INCI | Trade Name | (Comparative) | (Comparative) | (Inventive) |
| DISTEARDIMONIUM HECTORITE (and) PROPYLENE CARBONATE | BENTONE GEL ISD V | 25 | 25 | 25 |
| MQTPr RESIN (60% solids in isododecane) | | 32.5 | 32.5 | 32.5 |
| HYDROGENATED STYRENE/METHYL STYRENE/INDENE COPOLYMER | REGALITE™ R1100 CG | | 7.5 | 7.5 |
| ACRYLATES/POLYTRIMETHYL SILOXYMETHACRYLATE COPOLYMER | DOW CORNING® FA 4002 ID (40% active in isododecane) | | | 7.5 |
| WAXES | | 0.5 | 0.5 | 0.5 |
| COLOR PIGMENTS/ FILLERS | | 11.4 | 11.4 | 11.4 |
| ISODODECANE | | Q.S. | Q.S. | Q.S. |

What is claimed is:

1. A cosmetic composition comprising:
   (a) at least one MQTPr siloxane resin, present in the composition in an amount ranging from about 5% to about 50% by weight;
   (b) at least one silicone acrylate copolymer chosen from acrylate/polytrimethylsiloxymethacrylate copolymers, acrylate/dimethicone copolymers, and derivatives thereof, present in the composition in an amount ranging from about 0.1% to about 10% by weight;
   (c) at least one hydrogenated hydrocarbon resin chosen from hydrogenated styrene/methyl styrene/indene copolymers, hydrogenated polycyclopentadienes, and derivatives thereof, present in the composition in an amount ranging from about 1% to about 25% by weight;
   (d) at least one fatty phase;
   (e) optionally, at least one wax; and
   (f) optionally, at least one colorant;
   wherein the weight ratio, in the cosmetic composition, of the at least one silicone acrylate copolymer to the MQTPr siloxane resin ranges from about 1:8 to about 1:5.5; and
   wherein the weight ratio, in the cosmetic composition, of the at least one hydrogenated hydrocarbon resin to the MQTPr siloxane resin ranges from about 1:5 to about 1:1.5.

2. The cosmetic composition of claim 1 wherein the at least one MQTPr siloxane resin comprises the units:
   (a) $(R^1_3SiO_{1/2})_a$,
   (b) $(R^2_2SiO_{2/2})_b$,
   (c) $(R^3SiO_{3/2})_c$, and
   (d) $(SiO_{4/2})_d$,
   wherein:
   $R^1$, $R^2$, and $R^3$ are independently chosen from alkyl groups comprising from 1 to 8 carbon atoms, aryl groups comprising from 6 to 16 carbon atoms, carbinol groups, and amino groups,
   a has a value ranging from about 0.05 to about 0.5,
   b has a value ranging from about 0 to about 0.3,
   c has a value greater than about 0,
   d has a value ranging from about 0.05 to about 0.6,
   the sum of a+b+c+d is equal to 1, and
   greater than about 40 mole % of the $R^3$ groups in the siloxane resin are propyl groups.

3. The cosmetic composition of claim 1, wherein the weight ratio of the at least one MQTPr siloxane resin to the at least one silicone acrylate copolymer to the at least one hydrogenated hydrocarbon resin, respectively, is about 6.5:2.5:1.

4. The cosmetic composition of claim 1, wherein the weight ratio of the at least one hydrogenated hydrocarbon resin to the at least one silicone acrylate copolymer ranges from about 1:1 to about 4:1.

5. The cosmetic composition of claim 1, wherein the total solids content of the composition is less than about 50% by weight.

6. The cosmetic composition of claim 1, chosen from nail compositions, make-up compositions, mascara compositions, hair-care compositions, and sunscreen compositions.

7. A method of improving at least one property chosen from water- and/or oil-resistance, shine, malleability, adhesion, transfer resistance, comfort, and long wear properties in a cosmetic composition, said method comprising including in the cosmetic composition:
   (a) at least one MQTPr siloxane resin, present in the composition in an amount ranging from about 5% to about 50% by weight;
   (b) at least one silicone acrylate copolymer chosen from acrylate/polytrimethylsiloxymethacrylate copolymers, acrylate/dimethicone copolymers, and derivatives thereof, present in the composition in an amount ranging from about 0.1% to about 10% by weight; and
   (c) at least one hydrogenated hydrocarbon resin chosen from hydrogenated styrene/methyl styrene/indene copolymers, hydrogenated polycyclopentadienes, and derivatives thereof, present in the composition in an amount ranging from about 1% to about 25% by weight,
   wherein the at least one silicone acrylate copolymer is added to the cosmetic composition in a weight ratio relative to the MQTPr siloxane resin of from about 1:8 to about 1:5.5; and
   wherein the at least one hydrogenated hydrocarbon resin is added to the cosmetic composition in a weight ratio relative to the MQTPr siloxane resin of from about 1:5 to about 1:1.5.

8. The method of claim 7 wherein the at least one MQTPr siloxane resin comprises the units:
   (a) $(R^1_3SiO_{1/2})_a$,
   (b) $(R^2_2SiO_{2/2})_b$,
   (c) $(R^3SiO_{3/2})_c$, and
   (d) $(SiO_{4/2})_d$,
   wherein:
   $R^1$, $R^2$, and $R^3$ are independently chosen from alkyl groups comprising from 1 to 8 carbon atoms, aryl groups comprising from 6 to 16 carbon atoms, carbinol groups, and amino groups,
   a has a value ranging from about 0.05 to about 0.5,
   b has a value ranging from about 0 to about 0.3,
   c has a value greater than about 0,
   d has a value ranging from about 0.05 to about 0.6,
   the sum of a+b+c+d is equal to 1, and
   greater than about 40 mole % of the $R^3$ groups in the siloxane resin are propyl groups.

9. The method of claim 7, wherein the weight ratio of the at least one MQTPr siloxane resin to the at least one silicone acrylate copolymer to the at least one hydrogenated hydrocarbon resin, respectively, is about 6.5:2.5:1.

10. The method of claim 7, wherein the weight ratio of the at least one hydrogenated hydrocarbon resin to the at least one silicone acrylate copolymer ranges from about 1:1 to about 4:1.

11. The method of claim 7, wherein the total solids content of the composition is less than about 50% by weight.

12. A method of making up and/or enhancing the appearance of a keratinous substrate, said method comprising applying a cosmetic composition to the keratinous substrate, wherein the cosmetic composition comprises:
   (a) at least one MQTPr siloxane resin, present in the composition in an amount ranging from about 5% to about 50% by weight;
   (b) at least one silicone acrylate copolymer chosen from acrylate/polytrimethylsiloxymethacrylate copolymers, acrylate/dimethicone copolymers, and derivatives thereof, present in the composition in an amount ranging from about 0.1% to about 10% by weight;
   (c) at least one hydrogenated hydrocarbon resin chosen from hydrogenated styrene/methyl styrene/indene copolymers, hydrogenated polycyclopentadienes, and derivatives thereof, present in the composition in an amount ranging from about 1% to about 25% by weight;
   (d) at least one fatty phase;
   (e) optionally, at least one wax; and
   (f) optionally, at least one colorant;

wherein the weight ratio, in the cosmetic composition, of the at least one silicone acrylate copolymer to the MQTPr siloxane resin ranges from about 1:8 to about 1:5.5; and wherein the weight ratio, in the cosmetic composition, of the at least one hydrogenated hydrocarbon resin to the MQTPr siloxane resin ranges from about 1:5 to about 1:1.5.

* * * * *